(12) United States Patent
Wei et al.

(10) Patent No.: US 6,228,840 B1
(45) Date of Patent: May 8, 2001

(54) MELANOCORTIN RECEPTOR ANTAGONISTS AND MODULATIONS OF MELANOCORTIN RECEPTOR ACTIVITY

(76) Inventors: Edward T. Wei, 480 Grizzly Peak Blvd., Berkeley, CA (US) 94708; J. Mark Quillan, 623 Deancourt Crescent, Orleans, Ontario (CA), K4A 3G5; Wolfgang Sadée, 125 Lagunitas, Ross, CA (US) 94957; Guennady P. Vlasov, 2 Liniya, home 13/6, lodging 2 199034, Sankt Petersburg V-34 (RU)

( * ) Notice: Subject to any disclaimer, the term of this patent is extended or adjusted under 35 U.S.C. 154(b) by 0 days.

(21) Appl. No.: 09/031,902

(22) Filed: Feb. 27, 1998

(51) Int. Cl.[7] .................................................. A61K 38/08
(52) U.S. Cl. ................................ 514/16; 514/2; 530/329; 435/325
(58) Field of Search .............................. 514/16; 435/325; 530/329

(56) References Cited

U.S. PATENT DOCUMENTS

| | | | |
|---|---|---|---|
| 4,016,100 | 4/1977 | Suzuki et al. | 252/316 |
| 4,091,090 | 5/1978 | Sipos | 424/45 |
| 4,348,384 | 9/1982 | Horikoshi et al. | 424/101 |
| 5,126,327 | * 6/1992 | Takeuchi et al. | 514/18 |
| 5,480,869 | 1/1996 | Wei et al. | 514/16 |
| 5,482,930 | 1/1996 | Wei et al. | 514/13 |
| 5,514,670 | 5/1996 | Friedman et al. | 514/2 |

FOREIGN PATENT DOCUMENTS

| | | |
|---|---|---|
| 2193891 | 8/1987 | (GB) . |
| 97/47316 | 12/1997 | (WO) . |

OTHER PUBLICATIONS

Thomas et al. Peptides, 16(3), 547–50, Mar. 1995.*
Vlasov et al. Pept. 1996, Proc. Eur. Pept. Symp., 24th (1998), Meeting Date 1996, 877–878. Editor(s): Ramage, Robert; Epton, Roger. Publisher: Mayflower Scientific, Kingswinford, UK.*
Dowdy et al. Photodermatol., Photoimmunol. Photomed. (1995), 11(4), 143–8, Mar. 1995.*
Zhang et al. Clin. Med. Sci. J. 11(2) 63–68 Feb. 1996.*
Sawyer et al. Peptide Research, 2(1), 140–146, Jan. 1989.*
Dooley et al., "New, Highly Active Orphanin Receptor Ligands Identified Using Combinatorial Libraries," poster abstract from the 27th Meeting of the International Narcotics Research Conference, abstract TU13, Long Beach, California, 1996.

Hadley et al., "Melanocortin Receptors: Identification and Characterization by Melanotropic Peptide Agonists and Antagonists," *Pigment Cell Res.*, 9, pp. 213–234 (1996).

Henderson and McKnight, "The Orphan Opioid Receptor and Its Endogenous Ligand—Nociceptin/Orphanin FQ," *Trends in Pharmacological Sciences*, 18, pp. 293–300 (Aug. 1997).

Ollmann et al., "Antagonism of Central Melanocortin Receptors in Vitro and in Vivo by Agouti–Related Protein," *Science*, 278, pp. 135–138 (Oct. 3, 1997).

Quillan and Sadëe, "Dynorphin Peptides: Antagonists of Melanocortin Receptors," *Pharmaceutical Research* 14:6, pp. 713–719 (1997).

Quillan et al., "Combinatorial Diffusion Assay Used to Identify Topically Active melanocyte–Stimulating Hormone Receptor Antagonists," *Proc. natl. Acad. Sci. USA*, 92, pp. 2894–2898 (Mar. 1995).

Siegrist and Eberle, "Melanocortins and Their Implication in Melanoma," *TEM*, 6:4, pp. 115–120 (1995).

Siegrist et al., "Agouti Protein Inhibits Growth of B16 Melanoma Cells *in Vitro* by Acting through Melanocortin Receptors," *Biochem. Biophys. Res. Commun.*, 218, pp. 171–175 (1996).

Siegrist et al., "Interactions of α–Melanotropin and Agouti on B16 Melanoma Cells: Evidence for Inverse gonism of Agouti," *J. Recept. Signal. Transduct. Res.*, 17, pp. 75–98 (1997).

Berge et al., "Pharmaceutical Salts," *J. Pharm. Sci.*, 66:1, pp. 1–19 (1977).

Yang et al., "Effects of Recombinant Agouti–Signaling Protein on Melanocortin Action," *Mol. Endocrinol.*, 11, pp. 274–280 (1997).

* cited by examiner

*Primary Examiner*—Michael Borin

(57) ABSTRACT

The clinical outcome of disseminated melanoma is grim. Small molecular weight antagonists (preferably about seven amino acid residues) specific for MCR on melanoma cells are provided for the therapy of melanoma as well as in other conditions where modulation of MCR is of clinical significance. A particularly preferred antagonist is p-anisoyl-[D-Arg$^{6,9}$, D-Lys$^{11}$, D-Leu$^{12}$] dynorphin A(6–12)-NH$_2$, which is an excellent antagonist of the MCR-1 receptor.

9 Claims, 1 Drawing Sheet

```
                        SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 7 amino acids
         (B) TYPE: amino acid
         (D) TOPOLOGY: linear (ii) MOLECULE TYPE: protein (iii) HYPOTHETICAL: NO (iv) ANTI-SENSE: NO (ix) FEATURE:
         (A) NAME/KEY: Protein
         (B) LOCATION: 1
         (D) OTHER INFORMATION: /label= Arg /note= "The amino acid
             residue in position 1 is Arg or D-Arg"

(ix) FEATURE:
         (A) NAME/KEY: Protein
         (B) LOCATION: 3
         (D) OTHER INFORMATION: /label= Ile /note= "The amino acid
             residue in position 3 is either Ile or Ala"

(ix) FEATURE:
         (A) NAME/KEY: Protein
         (B) LOCATION: 6
         (D) OTHER INFORMATION: /label= Lys /note= "The amino acid
             residue in position 6 is either Lys or D-Lys"

(ix) FEATURE:
         (A) NAME/KEY: Protein
         (B) LOCATION: 7
         (D) OTHER INFORMATION: /label= Leu /note= "The amino acid
             residue in position 7 is either amidated Leu, D-Leu, or
             Ala."

(xi) SEQUENCE DESCRIPTION: SEQ ID NO:1:

Xaa Arg Xaa Arg Pro Xaa Xaa
1               5

(2) INFORMATION FOR SEQ ID NO:2:

(i) SEQUENCE CHARACTERISTICS:
         (A) LENGTH: 50 amino acids
         (B) TYPE: amino acid
         (D) TOPOLOGY: linear (ii) MOLECULE TYPE: protein (iii) HYPOTHETICAL: NO (iv) ANTI-SENSE: NO
```

(xi) SEQUENCE DESCRIPTION: SEQ ID NO:2:

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
                20                  25                  30

Ala Phe Cys Tyr Cys Arg Lys Leu Gly Thr Ala Met Asn Pro Cys Ser
            35                  40                  45

Arg Thr
    50

(2) INFORMATION FOR SEQ ID NO:3:

(i) SEQUENCE CHARACTERISTICS:
      (A) LENGTH: 6 amino acids
      (B) TYPE: amino acid
      (D) TOPOLOGY: linear   (ii) MOLECULE TYPE: protein  (iii) HYPOTHETICAL: NO   (iv) ANTI-SENSE: NO   (ix) FEATURE:
      (A) NAME/KEY: Peptide
      (B) LOCATION: 6

(xi) SEQUENCE DESCRIPTION: SEQ ID NO:3:

Arg Tyr Tyr Arg Trp Lys
1               5

(2) INFORMATION FOR SEQ ID NO:4:

(i) SEQUENCE CHARACTERISTICS:
      (A) LENGTH: 6 amino acids
      (B) TYPE: amino acid
      (D) TOPOLOGY: linear   (ii) MOLECULE TYPE: protein  (iii) HYPOTHETICAL: NO   (iv) ANTI-SENSE: NO   (xi) SEQUENCE DESCRIPTION: SEQ ID NO:4:

Arg Tyr Tyr Arg Trp Lys
1               5

(2) INFORMATION FOR SEQ ID NO:5:

(i) SEQUENCE CHARACTERISTICS:
      (A) LENGTH: 7 amino acids
      (B) TYPE: amino acid
      (D) TOPOLOGY: linear   (ii) MOLECULE TYPE: protein  (iii) HYPOTHETICAL: NO   (iv) ANTI-SENSE: NO   (xi) SEQUENCE DESCRIPTION: SEQ ID NO:5:

Arg Arg Ile Arg Pro Lys Leu
1               5

(2) INFORMATION FOR SEQ ID NO:6:

(i) SEQUENCE CHARACTERISTICS:

(A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Ala Arg Ile Arg Pro Lys Leu
1               5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

Arg Ala Ile Arg Pro Lys Leu
1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

Arg Arg Ala Arg Pro Lys Leu
1               5

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

Arg Arg Ile Ala Pro Lys Leu
1               5

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

Arg Arg Ile Arg Ala Lys Leu
1               5

(2) INFORMATION FOR SEQ ID NO:11:

(i) SEQUENCE CHARACTERISTICS:
             (A) LENGTH: 7 amino acids
             (B) TYPE: amino acid
             (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:11:

Arg Arg Ile Arg Pro Ala Leu
1               5

(2) INFORMATION FOR SEQ ID NO:12:

(i) SEQUENCE CHARACTERISTICS:
             (A) LENGTH: 7 amino acids
             (B) TYPE: amino acid
             (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:12:

Arg Arg Ile Arg Pro Lys Ala
1               5

MELANOCORTIN RECEPTOR ANTAGONISTS AND MODULATIONS OF MELANOCORTIN RECEPTOR ACTIVITY

FIELD OF THE INVENTION

The present invention relates to pharmaceutical compositions containing melanocortin receptor antagonists, and more particularly to methods for administering melanocortin receptor antagonists so as to modulate melanocortin receptor activity.

This invention was made with government support under Grant No. DA00091, awarded by the National Institutes of Health. The government has certain rights in this invention.

BACKGROUND OF THE INVENTION

Melanocytes are embryonically derived from the neural crest. These cells migrate to the skin during fetal development, sit on the basal lamina of the epidermis and interdigitate with basal cells via dendrites. Melanin is produced in the Golgi apparatus of the cell and this pigment is packaged (melanosomes) and delivered to keratinocytes and the hair follicle. In some cold-blooded vertebrates (frogs, fish, and reptiles), the cells synthesize melanosomes but do not pass it on to other cells. The melanosomes can move back and forth from the nucleus to the peripheral processes (dendrites) and this mechanism of dispersion and aggregation gives these animals the ability to change skin color from dark to light or vice versa. In cold-blooded vertebrates melanocytes are called melanophores.

α-, β-, and γ-Melanocyte-Stimulating-Hormone (MSH) and adrenocorticotropin (ACTH) are melanocortin receptor (MCR) peptide agonists derived (in humans) from post-translational processing of pro-opiomelanocortin (POMC). MCR are seven-transmembrane domain G-protein coupled receptors first discovered in 1992. Five subtypes have been cloned and named MCR-1 to MCR-5. There is consensus that MCR-1 exists on normal and neoplastic melanocytes and activation of these receptors results in increased melanogenesis (via G-protein stimulation, cAMP accumulation and tyrosinase activation). The MCR-4 receptor is implicated in body weight regulation. For example, inventors Gu et al. describe using melanocortin-4 receptor as a target to treat body weight disorders by modulating the activity of that receptor, WO 97/47316, published Dec. 18, 1997.

Melanoma is a tumor originating from unrestrained proliferation of melanocytes, which are pigment cells residing mainly in the epidermis. This tumor has an annual incidence in the United States of about 35,000 cases, with a mortality of approximately 7300 deaths (for 1997). The incidence of melanoma has been increasing significantly (with a 300 percent increase in the past 40 years). Currently, the lifetime risk of melanoma in the U.S. is approximately one percent. But in some countries such as Australia and New Zealand the lifetime risk is as high as $1/15$ or 6.7%.

The reason for the increased incidence of this disease is uncertain but may stem from greater recreational sun exposure, especially early in life, and a just released study suggests that sunscreen does not protect against skin cancer, including melanoma. Individuals most susceptible to development of melanoma are those with fair complexions, red or blond hair, blue eyes, and freckles and who are poor tanners and easy sunburners. Other factors associated with increased risk include family history of melanoma (approximately one in ten melanoma patients have a family member with melanoma) and the presence or excess of atypical moles.

Malignant melanoma is usually first detected as a change in size or shape of a pigmented area of the skin and confirmed by histological examination of the biopsy specimen. The five-year survival for localized disease (clinical stages I and II) is about 85 percent. For clinical stage III (clinically palpable nodes that contain tumor cells), a five-year survival of about 50 percent is noted when only one node is involved and about 15 to 20 percent when four or more nodes are involved. Five-year survival for clinical disseminated disease (stage IV) is less than five percent. Fortunately, the majority of melanomas are diagnosed in clinical stages I and II and melanomas less than 0.76 mm thick are usually cured by surgical removal (five-year survival rates range from 96 to 99 percent). On the other hand, metastatic melanoma to organs such as brain, liver, and lung, is associated with survival of less than one year.

Current treatment of the disseminated disease is usually palliative to improve the quality of life. Surgical excision of a single metastasis to the lung or to accessible brain sites can be associated with prolonged survival. Radiation therapy can provide local relief for recurrent tumors or metastatic sites. Patients who have advanced regional disease isolated to a limb may benefit from localized intra-arterial limb perfusion with chemotherapeutic agents. However, chemotherapy has a response rate of only 20 to 25 percent and rarely induces complete remission. The lack of response to traditional cancer treatments has led to many trials using agents such as retinoids, high-dosage chemotherapy with autologous bone marrow trans-plantation, antipigmentary agents, and antibodies conjugated to isotopes, drugs, and toxins. More recently, immunotherapy with interleukin-2 and α-interferon has been used. Marginally improved response rates have resulted from these experimental methods.

Wei and Thomas discovered that a number of dynorphin A peptides had the unusual property of preventing the increased vascular permeability of small blood vessels that occurs after tissue injury. This anti-inflammatory property of dynorphin A peptides and certain des-Tyr dynorphin A compounds and analogs is described in U.S. Pat. No. 5,482,930, issued Jan. 9, 1996.

Some MCR antagonists have been found in the agouti proteins (named after the South American rodent), which are 131 (mouse)/132 (human) amino acid proteins elaborated by hair follicle melanocytes and by brain tissue. The elaboration of agouti-signaling protein (ASP) determines the hair color of fur-coated animals. Agouti also antagonizes MCR-2 to MCR-5, but analyses of the binding coefficients do not indicate the clearcut characteristics of competitive antagonism which is found for MCR-1. (Yang et al., *Mol. Endocrinol.*, 11, pp. 274–280, 1997.) Siegrist et al. recently showed that ASP binds to the MCR-1 with an almost identical affinity to that of α-MSH, and that it had antiproliferative action with a half-maximal effective concentration of 13 nM. Agouti protein was also found to induce MC down-regulation. They also showed that ASP will inhibit the α-MSH-stimulated growth of B16-F1 mouse melanoma cells in culture. Siegrist et al., *J. Recept. Signal. Transduct. Res.*, 17, pp. 75–98 (1997); Siegrist et al., *Biochem. Biophys. Res. Commun.*, 218, pp. 171–175 (1996). However, an agouti-related protein (ARP) which was recently cloned from non-epidermal tissues had little effect on MCR-1 at concentrations up to 100 nM, although it did cause a dose dependent inhibition for MCR-3 and MCR-4. Ollmann et al., *Science*, 278, pp. 135–138 (1997).

SUMMARY OF THE INVENTION

It is an object of the present invention to provide antagonists to mammalian MCR receptors, particularly in the form of small or relatively small peptides.

The present invention provides a method for modulating the activity of a melanocortin receptor in which a melanocortin receptor antagonist is administered so as to be therapeutically useful in reducing the activity of melanocortin receptors. Thus, the present invention provides that small MCR antagonists may be used for the therapy of melanoma as well as in other conditions where modulation of MCR may be of clinical significance. One example of such uses to modulate is in the case of cancerous melanocytes (melanoma) in which MCR agonists stimulate growth and metastasis. Administration of an antagonist is useful in inhibiting the melanocytes. Another example is where the antagonist administered modulates the activity of MCR-4 receptors, so that modulation is useful in treating body weight disorders.

Thus, in an aspect of the present invention, a method of treating melanoma is provided in which a subject in need of treatment is administered a melanocortin receptor antagonist. The method inhibits melanocortin receptors on melanocytes when the melanocytes have administered thereto a melanocortin receptor antagonist having about seven amino acid residues and which is in an amount effective at concentrations of less than 250 nM so as to block the actions of α-melanocyte stimulating hormone.

Antagonists of the invention include peptides selected from:

(a) Xaa-Arg-Xaa-Arg-Pro-Xaa-Xaa (SEQ ID NO:1), such as dynorphin A(6–12), where $Xaa^6$ is Arg or D-Arg, Ala or D-Ala, $Xaa^8$ is Ile or Ala, $Xaa^{11}$ is Lys or D-Lys, and $Xaa^{12}$ is amidated Leu, D-Leu, or Ala. The Arg in the sixth and/or ninth position is preferably in the D-Arg stereoconfiguration, which substantially increases potency. Additional, particularly preferred modifications are where the peptides have an acylated amino terminus, or an anisoylated (methoxybenzoyl) N-terminus, and have an amidated carboxyl terminus (e.g. amidated Leu);

(b) a mystixin having the sequence $T_N$-$A_1$-$A_2$-$A_3$-$A_4$-$A_5$-$A_6$-$T_C$, where $T_N$ is an amino terminal portion having a molecular weight less than about 600 daltons and is selected to convey resistance against enzymatic degradation. A preferred $T_N$, for example, is N-acetylated Tyr(Me) or methoxybenzoyl; $A_1$ is D- or L-arginine and D-lysine; $A_2$ is lysine or arginine; $A_3$ is leucine or isoleucine; $A_4$ is leucine, isoleucine, methionine, or valine; $A_5$ is methoxybenzoyl-ethyl-Gly, methoxybenzoylmethyl-D-Ala, Tyr(Me), Trp, Tyr, Leu, Lys, Arg, 4' substituted Phe (4'F, 4'I, 4'Cl, 4'$NO_2$), D-His, D-Lys, D-Arg, D-Leu, D-Pro, or D-Trp; $A_6$ is isoleucine; with the proviso that not all of the $A_1$–$A_6$ are in the L-configuration; and $T_C$ is isoleucineamide, D-leucineamide, D-valineamide; or (c) is a compound having the sequence Arg-Tyr-Tyr-Arg-Trp-Lys (SEQ ID NO:4) or Arg-Try-Try-Arg-D-Trp-Lys which may include the modifications as described in (a).

In another aspect of the present invention, a method of modulation, particularly in treating body weight disorders, comprising administering an antagonist selective for the MCR-4 receptor. Antagonists of the invention for the MCR-4 receptors in accordance with the invention include an agouti-related protein fragment (83-132), which is preferably amidated.

Although therapeutic uses are contemplated, particularly because there have been so few known antagonists of melanocortin receptors known to date, the antagonists herein described will also be useful in drug screening assays.

Aspects of the invention will be illustrated through inhibition of melanocyte cells in which a substance decreases the activity of a melanocortin receptor agonist (i.e. α-melanocyte stimulating hormone, or α-MSH) on frog melanophores or on mammalian cells transfected with melanocortin receptors. The inhibition constant ($K_i$), given in units of concentration, which is defined as the concentration of the antagonist which doubles the amount of agonist required to produce the same degree of effect, is computed; or the inhibitory concentration of the antagonist ($IC_{50}$), which reduces by 50% the activity of a fixed concentration of agonist (usually 200 to 600 picoM of α-MSH), is obtained. Particularly preferred antagonists for therapeutic utility have value of $K_i$ or $IC_{50}$ of less than 250 nM.

DETAILED DESCRIPTION OF THE PREFERRED EMBODIMENTS

Hormone receptors are increasingly of interest as pharmaceutical targets, and the use of hormone-receptor antagonists for therapy is well-established in the treatment of breast and prostate cancers. Primary examples are tamoxifen and flutamine, which are antagonists of the steroidal estrogen and androgen receptors, respectively (Goodman and Gilman, Pharmacological Basis of Therapeutics, 1997).

We have discovered certain peptides that are antagonists against mammalian melanocortin receptors and which are useful in modulating the activity of these receptors. Thus, two of us have recently discovered that some dynorphin A peptides antagonize the human MCR-1, MCR-3, and MCR-4 receptors (Quillan and Sadée, *Pharm. Research*, 14, pp. 713–719, 1997). Thus, dynorphin A(1–13) -$NH_2$ was found to be the most potent of a series with an $IC_{50}$ of 110 to 145 nM (against 600 pM α-MSH). Further shortening of the carboxyl terminal end was found to cause reduction in antagonist potency. Analogs of [des-Tyr] dynorphin A were also tested. Dynorphin (2–17) was found to have an $IC_{50}$ value of 190 nM (against 600 pM α-MSH). Dynorphin A(6–17) was also tested for antagonist activity, but was found to be inactive. Antagonists useful in the subject invention further include dynorphin A(6–12), mystixins, an agouti-related protein (ARP) fragment, and some ligands for an orphan opioid receptor. These will now be more fully described.

Dynorphin A Fragments

We have surprisingly discovered that dynorphin A(6–12) and some variations thereof are particularly excellent antagonists of the MCR-1 receptor. Dynorphin fragments of the present invention, which include dynorphin A(6–12), have the general structure shown by Formula 1 (SEQ. ID NO:1):

FORMULA 1 where $Xaa^6$ is Arg or D-Arg, Ala or D-Ala, $Xaa^8$ is Ile or Ala, $Xaa^{11}$ is Lys or D-Lys, and $Xaa^{12}$ is amidated Leu, D-Leu, or Ala. The Arg in the sixth and/or ninth position is preferably in the D-Arg stereoconfiguration, which substantially increases potency. Additional, particularly preferred modifications are where the peptides have an acylated amino terminus, or an anisoylated N-terminus, and have an amidated carboxyl terminus (e.g. amidated Leu). Of the various modifications or substituents possible with peptides in accordance with the present invention, the most potent modification appears to be the attachment of an anisoyl (methoxybenzoyl) group to the N-terminus. The position of the methoxy group on the benzene ring does not appear to be a critical determinant of activity as para, meta, and ortho anisoyl- substituted analogs exhibited similar potencies. The p-nitrobenzoyl analog was as active as the anisoyl analogs. Other alternative modifications, such as p-methylpenylacetyl, p-toylacetyl, phenoxyacetyl, and p-aminobenzoyl derivatives, are possible.

In the case of dynorphin A(6–12), Xaa is arginine at position 6, isoleucine at position 8, lysine at position 11, and leucine at position 12. A particularly preferred peptide of the invention with good potency is sometimes referred to as "SQW-5," which is p-anisoyl-[D-$Arg^{6,9}$, D-$Lys^{11}$, D-$Leu^{12}$] dynorphin A(6–12)-$NH_2$.

Figure 1:
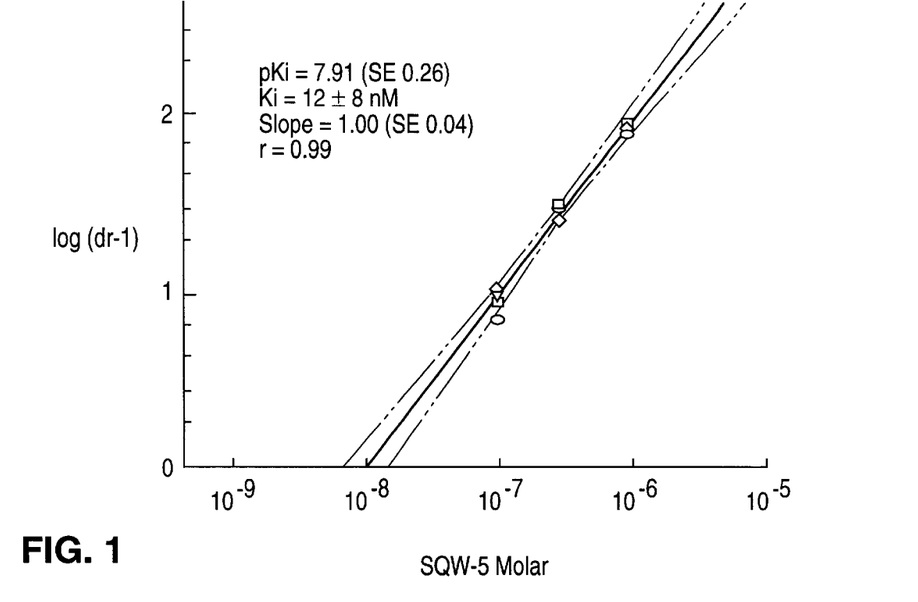
FIG. 1 graphically illustrates the activity of an dynorphin A(6–12)-amide analog (called "SQW-5") in the form of a Schild Plot where the slope of the regression line is near unity; and, FIG. 2 graphically illustrates the antagonist activity of agouti-related protein (83–132)-amide where the agonist log-concentration-response curve is shifted to the right without any substantial change in slope or maximal, which is indicative of reversible competitive antagonism.

FIG. 1 graphically illustrates the activity a dynorphin A(6–12)-amide analog, SQW-5, which antagonizes the stimulatory effects of α-MSH on melanin dispersion in Xenopus frog melanophores. The presentation of data is in the form of a Schild Plot wherein the goal is to obtain a inhibitory constant ($K_i$) which estimates the antagonist potency of the test compound. At varying doses of the antagonist, the dose-ratio for the amount α-MSH to produce darkening of the melanophores is shifted. A regression analysis yields the $K_i$ value at the intercept on the abscissa. The $K_i$ value is defined as the concentration of antagonist, in this case 12 nM of SQW-5, which is sufficient to require a doubling of the concentration of α-MSH required to produce an equivalent effect. The slope of the regression line is near unity, which is indicative of reversible competitive antagonism.

Although less potent than the particularly preferred dynorphin A(6–12) analog, dynorphin A(1–13)-amide is another antagonist useful in practicing the subject invention.

Mystixins

Mystixins contain the sequence -Arg-Lys-Leu-(Leu/Met)-X-Ile-(Leu/D-Leu)-$NH_2$ where X may be an anisolyated glutamic derivative (A*) or other aromatic residues. U.S. Pat. No. 5,480,869, issued Jan. 2, 1996, inventors Wei and Thomas describes mystixins that have anti-inflammatory properties and are useful in inhibiting vascular leakage in injured tissue. These mystixins have now been found to be antagonists against mammalian MCR-1 receptors.

Thus, useful mystixins have the sequence $T_N$-$A_1$-$A_2$-$A_3$-$A_4$-$A_5$-$A_6$-$T_C$, where $T_N$ is an amino terminal portion having a molecular weight less than about 600 daltons and is selected to convey resistance against enzymatic degradation. A preferred TN, for example, is N-acetylated Tyr(Me) or methoxybenzoyl; $A_1$ is D- or L-arginine and D-lysine; $A_2$ is lysine or arginine; $A_3$ is leucine or isoleucine; $A_4$ is leucine, isoleucine, methionine, or valine; $A_5$ is methoxybenzoyl-ethyl-Gly, methoxybenzoylmethyl-D-Ala, Tyr(Me), Trp, Tyr, Leu, Lys, Arg, 4' substituted Phe (4' F, 4' I, 4' Cl, 4'$NO_2$), D-His, D-Lys, D-Arg, D-Leu, D-Pro, or D-Trp; $A_6$ is isoleucine; with the proviso that not all of the $A_1$–$A_6$ are in the L-configuration; and Tc is isoleucineamide, D-leucineamide, D-valineamide.

Some other of the melanocortin receptor antagonists of the present invention have also previously been shown to have anti-inflammatory properties. It is not known whether the previously known anti-inflammatory properties are related to antagonism on melanocortin receptors. Indeed, as will be hereinafter discussed, in some instances peptides useful in accordance with the present invention as melanocortin receptor antagonists do not have significant anti-inflammatory properties.

Agouti-Related Protein (ARP) Fragment

In practicing the present invention, we have found that the amidated carboxyl-terminal ARP fragment (83–132)-$NH_2$ is potently active with an inhibitory equilibrium disassociation constant ($K_i$) of 0.7 nM for the frog melanophore receptor. The sequence of this fragment (SEQ. ID NO:2) is:

SSRRCVRL HESCLGQQVP CCDPCATCYC RFFNAFCYCR KLGTAMNPCS RT

Human ARP and human ASP are two proteins found in tissues which have the property of antagonizing melanocortin receptors. Currently, these proteins are made by recombinant methods but the structural features of the proteins which determine MCR antagonism are not understood.

As will be further described, the peptide fragments of human ARP consisting of the amidated form of (83–132) were synthesized on an Applied Biosystem's 433A automated peptide synthesizer (Foster City, Calif.) using para-methyl-benzylhydrylamine resin as the solid support and standard solid-phase F-moc methods. N-terminal F-moc amino acids were deprotected with 20% piperidine in dimethylformamide and coupled with o-benzotriazole-N,N,N', N'-tetramethyl-uronium hexa-fluorophosphate in 1-hydroxybenzotriazole. Peptide was cleaved from resin with hydrogen fluoride, washed with diethyl ether, extracted with water/acetonitrile, and cyclized at pH 8.5. Preparatory HPLC separations of the extracts yielded a peptide which was 99% pure by analytical HPLC. MALDI-TOF mass spectra of the linear fragments gave molecular weights which corresponded to theoretical values. As yet, the precise arrangement of disulfide bridges within ARP and its C-fragment, which contain 11 and 10 Cys, respectively, are undetermined.

Figure 2:
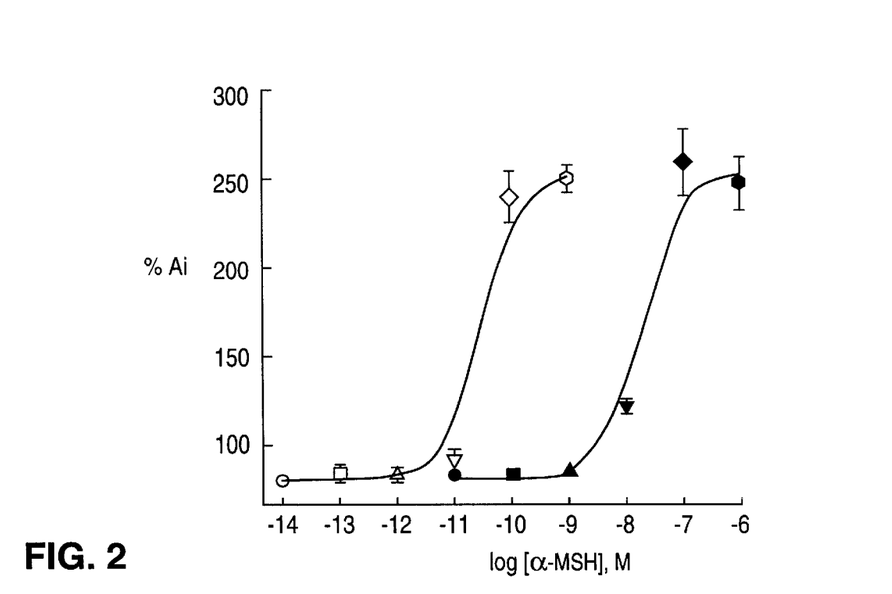

In FIG. 2, the activity of ARP-(83–132)-$NH_2$ as an antagonist of α-MSH (0.1 nM) MC in frog melanophores is shown. The $EC_{50}$ of α-MSH alone is 0.03 nM. In the presence of ARP fragment, 30 nM, the $EC_{50}$ of α-MSH is increased to 19 nM. This parallel shift is indicative of competitive binding for the MC receptor site.

A Schild plot regression analysis of ARP (83–132)-$NH_2$ illustrates the potency of this peptide fragment. The $K_i$ value of 0.21 nM is less than that of dynorphin A peptides and mystixin peptides, but comparable to the intact protein.

Ligands for an Orphan Opioid Receptor

An orphan opioid receptor (ORL1) was recently identified and its endogenous ligand characterized and called nociceptin/orphanin FQ. Nociceptin/orphanin FQ is a 17-amino acid residue peptide with structural homology to dynorphin A(1–17). C. T. Dooley, C. Spaeth, L. Toll, and R. A. Houghten presented an abstract at the 27th Meeting of the International Narcotics Research Conference, abstract TU13, Long Beach, Calif. 1996; cited in detail in Trends in *Pharmacological Sciences,* 18, pp. 293–300 (August 1997), (article by G. Henderson and A. T. McKnight, "The Orphan Opioid Receptor and its Endogenous Ligand—Nociceptin/Orphanin FQ") in which they used combinatorial libraries of hexapeptides to screen for and to find ligands for the ORL1 receptor. A ligand was identified, Ac-Arg-Tyr-Tyr-Arg-Trp-Lys-NH$_2$, SEQ. ID NO:3, which exhibited affinity and agonist activity at the ORL1 receptor.

We have now found that this ligand, as well as several analogs prepared with modifications to the N-terminus thereof, exhibits activity as a melanocortin receptor antagonists. One of these ligands has a potency similar to dynorphin A(1–13)-NH$_2$. These data are shown in Example 4.

EXPERIMENTAL

A standard procedure for evaluating MCR antagonists is to use cells which bear such receptors and are activated by α-MSH, and to examine the shift in concentration-response curves to α-MSH in the presence of the antagonists. Examples of such methods are given in Quillan and Sadée (*Pharm. Res.*, 14, pp. 713–719, 1997) and Ollmann et al. (*Science*, 278, pp. 135–138, 1997).

Pure cultures of melanophores derived from *Xenopus laevis* embryos have been used to study MCR. Xenopus melanophore cell cultures are maintained in 5 parts Leibovitz's L-15 medium (Gibco), 2 parts FBS, 3 parts deionized-distilled H$_2$O, and phosphate-buffered saline. Cultured melanophore cells retain their ability to aggregate (lightened state) or disperse (darkened state) cytoplasmic pigment vesicles in response to hormonal stimulation, melatonin causes aggregation whereas α-MSH, vasotocin, histamine, norepinephrine, and serotonin cause dispersion. Concentration-response curves were measured in melanophores by quantifying the change in absorbance at 630 nm through a monolayer of cells using a BT2000 Microplate Reader (FisherBiotech, Pittsburgh, Pa.) after treatment with test compounds, and curves were fit using a logistic equation. Initial absorbance ($A_i$) was measured upon addition of test compounds after 90 minutes pretreatment with carrier alone (7 parts L-15 medium in 3 parts distilled-deionized H$_2$O containing 0.5% (w/w) bovine serum albumin), or carrier plus 1 nM melatonin, to initiate tests from either the dispersed state (high absorbance) or an aggregated state (low absorbance), respectively.

A second method for studying MCR antagonists is to use mammalian cells stably transfected with the cDNA for various human MCR. These transfected cells manifest an increased CAMP response to α-MSH stimulation and agents which antagonize MCR will block this stimulating effect of α-MSH. The inhibitory effects of antagonists can be quantified by the change in the effective concentration (EC$_{50}$) of α-MSH i the presence of antagonist, or by computation of K$_i$ value by a Schild regression analysis.

EXAMPLE 1

Dyn A(6–12) Analogs Demonstrate MCR Antagonist Activity by Blocking α-MSH Activation of Xenopus MC Receptors Dynorphin A peptides have no direct stimulatory effect on MC receptors endogenous to xenopus melanophores but inhibited activation of these receptors by α-MSH. To compare the relative potency of various dynorphin A(6–12) analogs, IC$_{50}$ measurements were made against a fixed concentration (600 pM) of α-MSH. Melanophores were used because dynorphin peptides were of comparable potency at both frog and human MC receptors.

A graphical illustration for the determination of the antagonist potency, as measured by Ki, is shown for the analog SQW-5 (FIG. 1). The melanophores in the presence of 600 pM of α-MSH have an absorbance 200% greater than the initial value ($A_i$). Increasing concentrations of SQW-5 block the α-MSH effect and the increased light passing through the aggregated melanosomes is measured by the decrease in absorbance. The logistic fit of the data gives the IC$_{50}$ value which is the statistically most reliable point for measurement of potency.

None of the dynorphin A(6–12) analogs tested caused stimulation (darkening) of melanophores, but most were active as antagonists against α-MSH with IC$_{50}$ values ranging from 17 to 1600 nM. The results are shown in Table 1. The more potent analogs (SQW-1, 4, 5, 6) with IC$_{50}$ of 17 to 42 nM were active as anti-edema agents, but the correlation of anti-edema to MCR antagonist potencies was weak. For example, the good MCR antagonist potency of SQW-6, 8, and 13 was not matched by a corresponding enhanced potency in suppression of edema. In analogs singly substituted with alanine, reduction of the number of side-chain carbons in residue 11 significantly decreased MCR antagonist potency. Substitution of the L-Arg residues by the D-Arg isomer retained the MCR antagonist activity and the anti-edema potency. These analogs have not been previously described.

To further quantify the activity of candidate prototypes, dose-response curves were measured in the presence of several concentrations of antagonists and Schild plots were used to estimate equilibrium dissociation K$_d$ values for SQW-1 and SQW-5. This analysis yielded K$_i$ values of 27 and 12 nm, respectively, which are significantly lower than values of 71 and 79 nM found for dynorphin A(1–13)-NH$_2$ and dynorphin A(2–13), respectively. The Schild regression slopes for SQW-1 and SQW-5 are almost unity which indicate a mechanism of competitive inhibition at the MCR for the two analogs.

Dynorphin A(2–17) lowers blood pressure of anesthetized rats. It was therefore of interest to determine if a prototype dynorphin A(6–12) analog, with a lower molecular weight, would exhibit similar hypotensive activity. The dose-effect curves of dynorphin A(2–17) and p-anisoyl-[D-Leu$^{12}$] dynorphin A(6–12)-NH$_2$ on the mean arterial pressure of pentobarbital-anesthetized rats were compared. Analysis of the integrated hypotensive activities, measured by the area-under-curve, for the two peptide, indicated that, on a molar basis, the two peptides had similar hypotensive activities. The potencies for anti-edema and hypotensive actions were not directly correlated as dynorphin A(2–17) was at least twice more active than p-anisoyl-[D-Leu$^{12}$] dynorphin A(6–12)-NH$_2$ as an anti-edema agent. The anti-edema activities were detectable at doses which did not produce significant hypotension.

The selectivity of the MC receptor antagonism by dynorphin A(6–12) analogs was examined. Under the same experimental conditions, the dispersion of melanin initiated by norepinephrine, serotonin, and vasotocin were not inhibited by SQW-1. Peptides which inhibit heat-induced edema such as human CRH, urocortin, sauvagine, xenopsin, and a neurotensin(8–13) analog, D-Arg-Arg-Pro-Trp-Ile-Leu, were relatively inactive in the frog MCR assay with IC$_{50}$ values of >10 μM.

TABLE 1

Melanocortin receptor antagonist activities of anisoyl-dynorphin A(6–12) —NH$_2$ analogs

| | N-terminus | 6 | 7 | 8 | 9 | 10 | 11 | 12-amide | MCR IC$_{50}$ nM | Anti-Inflammatory ED$_{50}$ μmoles/kgi |
|---|---|---|---|---|---|---|---|---|---|---|
| SQW-1 | p-anisoyl- | Arg- | Arg- | Ile- | Arg- | Pro- | Lys- | D-Leu- | 29 ± 1 | 0.21 |
| SQW-6[a] | m-anisoyl- | Arg- | Arg- | Ile- | Arg- | Pro- | Lys- | Leu- | 42 ± 2 | 0.51 |
| SQW-7[b] | m-anisoyl- | Ala- | Arg- | Ile- | Arg- | Pro- | Lys- | Leu- | 110 ± 8 | >1 |
| SQW-8[c] | m-anisoyl- | Arg- | Ala- | Ile- | Arg- | Pro- | Lys- | Leu- | 75 ± 3 | >1 |
| SQW-9[d] | m-anisoyl- | Arg- | Arg- | Ala- | Arg- | Pro- | Lys- | Leu- | 155 ± 14 | 0.65 |
| SQW-10[e] | m-anisoyl- | Arg- | Arg- | Ile- | Ala- | Pro- | Lys- | Leu- | 187 ± 20 | 1.02 |
| SQW-11[f] | m-anisoyl- | Arg- | Arg- | Ile- | Arg- | Ala- | Lys- | Leu- | 188 ± 68 | 1.05 |
| SQW-12[g] | m-anisoyl- | Arg- | Arg- | Ile- | Arg- | Pro- | Ala- | Leu- | 1600 ± 1500 | 0.98 |
| SQW-13[h] | m-anisoyl- | Arg- | Arg- | Ile- | Arg- | Pro- | Lys- | Ala- | 62 ± 1 | 2.39 |
| SQW-2 | p-anisoyl- | Arg- | Arg- | Ile- | D-Arg- | Pro- | D-Lys- | D-Leu- | 114 ± 15 | 0.085 |
| SQW-3 | p-anisoyl- | Arg- | D-Arg- | Ile- | D-Arg- | Pro- | D-Lys- | D-Leu- | 156 ± 15 | 0.095 |
| SQW-4 | p-anisoyl- | D-Arg- | D-Arg- | Ile- | D-Arg- | Pro- | D-Lys- | D-Leu- | 17 ± 6 | 0.200 |
| SQW-5 | p-anisoyl- | D-Arg- | Arg- | Ile- | D-Arg- | Pro- | D-Lys- | D-Leu- | 42 ± 8 | 0.060 |

Anisoyl = methoxybenzoyl
*antagonism of α-MSH darkening of frog melanophores
**based on suppression of heat-induced edema in the anesthetized rat's paw Schild Plots (concentration of the antagonist is varied and the dose-ratio (DR) computed)

SQW-1 pK$_i$=7.57±0.1, K$_i$=27±6 nM

SQW-5 pK$_i$=7.91±0.3, K$_i$=12±8 nM

EXAMPLE 2

Melanocortin Receptor Antagonist Activities of SOW-5 and Mystixin-7 in Cells Transfected with the Human MCR-1 and MCR-4 Receptors Human embryonic kidney (HEK-293) cells were maintained in modified Eagle's medium (DMEM/H-16/F-12) with 10% fetal calf serum (FBS), 100 U/mL penicillin "G" and 100 μg/mL streptomycin (P/S; Gemini). Transfections were performed using CDNA containing the human MCR-1 receptor (pcDNAI/NEO hMC1), or MCR-4 (pcCMV.hMC4) receptors. HEK-293 cells are stably transformed with the human MCR-1 and MCR-4 receptors by electroporating 20 μg of plasmid cDNA using a Gene Pulser transfection apparatus (450 V, 960 μF; BioRad, Hercules, Calif.). After six days, stable MC clonal cell lines were selected by addition of 400 μg/ml G-418 to the medium and kept frozen for future use.

Cyclic-AMP and Concentration-Response Measurements

Peptide concentration-response measurements are made in HEK-293 cells by quantifying cAMP levels using a [8-$^3$H]-cAMP kit from Amersham. Briefly, cells transfected with MC receptors, plated to confluency in 96-well tissue culture plates, are rinsed for 1 hr with 70% (vol/vol) L-15 medium containing 0.5% bovine serum albumin. After a 30 min exposure to test ligands, HEK-293 cells are rinsed twice with ice-cold 70% phosphate-buffered saline (0.07 g/L CaCl$_2$, 0.07 g/L MgCl$_2$.6H$_2$O, 0.14 g/L KH$_2$PO$_4$, 1.51 g/L Na$_2$HPO$_4$.7H$_2$O, 0.14 g/L KCl, 5.6 g/L NaCl, pH 7.4), and intracellular CAMP extracted with 1 mL of 60% (vol/vol) ethanol. Cellular debris was separated from extracted samples by centrifugation, 400 μL aliquots of the supernatant lyophilized, and total cAMP content quantified by isotope counting.

Results

Addition of α-MSH to the transfected cells stimulates the accumulation of cyclic AMP from a basal level of about 2 pM per well to 4 to 6 pM per well. The effective concentration of α-MSH for 50% stimulation (EC$_{50}$) is computed in the presence or absence of the test substance—in this case, 5 μM of either SQW-5 or mystixin-7. These peptides produced a parallel shift to the right for the EC$_{50}$ of α-MSH, indicating competitive antagonism at the transfected MCR-1 and MCR-4 (for SQW-5) receptors.

TABLE 2

| Treatment: 5 μM peptide antagonist | MCR-1 transfected EC$_{50}$ ± SE nM | MCR-4 transfected EC$_{50}$ ± SE nM |
|---|---|---|
| α-MSH | 0.13 ± 0.08 | 0.6 ± 0.3 |
| α-MSH + SQW-5 | 14 ± 5* | 18 ± 6* |
| α-MSH + mystixin 7 | 11 ± 9* | NA |

*statistically significant, P<0.01

The antagonist activities of the mystixin analogs are shown in Table 3.

TABLE 3

| | Mystixin 7 mer-Peptides | MCR Antagonism IC$_{50}$ nM in Xenopus | Anti-Inflammatory ED$_{50}$ mg/kg i.v.* |
|---|---|---|---|
| | Alanine-Walk | | |
| S-167 | p-anisoyl-Ala-Lys-Leu-Leu-D-Thi-Ile-o-Leu-NH$_2$ | 1200 ± 500 | >2 |
| S-166 | p-anisoyi-Arg-Ala-Leu-Leu-o-Thi-Ile-o-Leu-NH$_2$ | 1200 ± 1500 | >2 |
| S-160 | p-anisoyl-Arg-Lys-Ala-Leu-o-Thi-Ile-o-Leu-NH$_2$ | 197 ± 12 | 0.18 (0.07–0.49) |
| S-165 | p-anisoyl-Arg-Lys-Leu-Ala-D-Thi-Ile-D-Leu-NH$_2$ | 282 ± 39 | 0.046 (0.015–0.14) |
| S-164 | p-anisoyl-Arg-Lys-Leu-Leu-D-Ala-Ile-D-Leu-NH$_2$ | 26 ± 16 | 0.42 (0.18–0.96) |

TABLE 3-continued

| | Mystixin 7 mer-Peptides | MCR Antagonism IC$_{50}$ nM in Xenopus | Anti-Inflammatory ED$_{50}$ mg/kg i.v.* |
|---|---|---|---|
| S-163 | p-anisoyl-Arg-Lys-Leu-Leu-o-Thi-Ala-o-Leu-NH$_2$ | 234 ± 149 | 0.067 (0.030–0.15) |
| S-162 | p-anisoyl-Arg-Lys-Leu-Leu-D-Thi-Ile-D-Ala-NH$_2$ | 43 ± 26 | 0.24 (0.11–0.50) |
| | Variations on Residue 5 | | |
| mystixin-7 (S-21) | p-anisoyl-Arg-Lys-Leu-Leu-o-Thi-Ile-o-Leu-NH$_2$ | 237 ± 79 | 0.02 (0.014–0.059) |
| S-114 | p-anisoyl-Arg-Lys-Leu-Leu-o-Nal-Ile-o-Leu-NH$_2$ | 166 ± 274 | 0.38 (0.16–0.91) |
| S-116 | p-anisoyl-Arg-Lys-Leu-Leu-o-Tyr-Ile-o-Leu-NH$_2$ | 77 ± 57 | 0.080 (0.03–0.20) |
| S-117 | p-anisoyl-Arg-Lys-Leu-Leu-o-Trp-Ile-o-Leu-NH$_2$ | 22 ± 13 | 0.16 (0.050–0.40) |
| S-118 | p-anisoyl-Ala-Lys-Leu-Leu-D-Thi-Ile-D-Leu-NH$_2$ | 96 ± 53 | 0.035 (0.012–0.10) |

*Suppression of heat-induced edema in the anesthetized rat's paw

EXAMPLE 3

HEK-293 cells were maintained and transfected As described in Example 2. HEK-293 cells were stably transformed with the human MCR-1, MCR-3, and MCR-4 receptors by electroporating 20 µg of plasmid CDNA (≈8×10$^6$ cells per 800 µL in 100% Ca$^{2+}$/Mg$^{2+}$-free phosphate-buffered saline in 0.4 cm cuvettes at 400V, and 960 µF). After six days stable MC clonal cell lines were selected by addition of 400 µg/mL G-418 (Geneticin; Gibco/BRL) to the medium.

Concentration response measurements were made also as described in Example 2, but in Xenopus fibroblasts, COS-7, HEK-293, and Y1 cells.

Dynorphin peptides were found to inhibit α-MSH-mediated activation of three recombinant human MC receptors stably expressed in HEK cells. The opioid congener dynorphin A(1–13)-NH$_2$ (30 µM) produced a 300-to 1500-fold shift in concentration-response curves to α-MSH at each of the MCR-1, MCR-3, and MCR-4 receptor subtypes tested. The EC$_{50}$ for α-MSH alone was 1.4±0.6, 4.2±2.1, and 3.0±1.7 nM, for the MCR-1, MCR-3, and MCR-4 receptors respectively, and increased to 2,100±900, 1,600±1,100, and 2,000±1,200 nM, respectively, in the presence of 30 µM dynorphin A(1–13)-NH$_2$. Shifts in concentration-response curves to α-MSH were not blocked by naloxone (10 µM), indicating that opioid receptors are not involved. Dynorphin induced shifts in α-MSH response curves expressed as dose ratios were used to compare relative dynorphin effects at a number of MC and other receptor types. Dose ratios for the MCR-1, MCR-3, and MCR-4 receptors ranged from approximately 500 to 1000.

Since the non-opioid effects of dynorphin include those produced by [des-Tyr]dynorphin metabolites, compounds which do not bind opioid receptors, we also tested dynorphin A(2–13) interactions with MC receptors. At each receptor subtype, dynorphin A(2–13) produced significant shifts in concentration-response curves that were 3 to 5 times smaller than dynorphin A(1–13)-NH$_2$. Dose ratios calculated from α-MSH dose-response curves measured in the presence and absence of 30 µM dynorphin A(2–13) indicated shifts of 250±31, 128±44, and 147±13 for the MCR-1, MCR-3, and MCR-4 receptors, respectively. Therefore, dynorphin A(2–13) was an effective antagonist of α-MSH, but was of slightly lower potency than dynorphin A(1–13)-NH$_2$.

Dynorphin A(1–13)-NH$_2$ and dynorphin A(2–13) were also tested for their ability to inhibit the ACTH (MCR-2) receptor endogenous to murine Y1 adrenocortical cells. At 30 µM, dynorphin A(2–13 and dynorphin A(1–13)-NH$_2$ shifted the concentration-response curve of ACTH-(1–24) approximately 15 and 200-fold to the right, respectively. The EC$_{50}$ of ACTH-(1–24) alone was 1.8±1.2 nM, and 28±13 and 364±112 nM in the presence of 30 µM dynorphin A(2–13) and dynorphin A(1–13)-NH$_2$, respectively. Dynorphin's interaction with the MCR-2 receptor is significant but less potent than observed with the MCR-1, MCR-3, and MCR-4 receptors. The shift in the ACTH concentration-response curve suggests an estimated K$_d$ for dynorphin A(1–13)-NH$_2$ in the submicromolar range. α-MSH by itself, up to concentrations of 10 µM, was not effective in stimulating cAMP accumulation in Y1 cells, and dynorphin A(1–13)-NH$_2$ did not significantly affect basal, or inhibit forskolin (3 µM) stimulated, cAMP production.

In Cos-7 cells, cells that contain an atypical MC receptor (27), α-MSH elevated cAMP production, but did so with relatively low potency (EC$_{50}$~80 nM). This EC$_{50}$ value was shifted ~50-fold by 30 µM dynorphin A(1–13)-NH$_2$, demonstrating that dynorphin A(1–13)-NH$_2$ also antagonizes the MC receptor subtype found in Cos-7 cells, but with somewhat lower potency (K$_4$~1 µM).

EXAMPLE 4

As earlier described, the ligand SEQ. ID NO:3 has been identified as exhibiting affinity and agonist activity at the ORL1 receptor. This and several other analogs were prepared and tested for activity as melanocortin receptor antagonists. These are shown below.

| | Analog | IC$_{50}$ nM in Frog Melanophore Assay |
|---|---|---|
| 1 | Ac-Arg-Tyr-Tyr-Arg-Trp-Lys-NH$_2$ | 1050 ± 170 |
| 2 | Ac-Arg-Tyr-Tyr-Arg-D-Trp-Lys-NH$_2$ | 867 ± 85 |
| 3 | p-Anisoyl-Arg-Tyr-Tyr-Arg-D-Trp-Lys-NH$_2$ | 175 ± 27 |

All three peptides exhibited at least some activity as melanocortin receptor antagonists, with analog (3) having the best potency. Dynorphin A(1–13)-NH$_2$, which was also tested, had an IC$_{50}$ of 145±14 nM.

The peptide antagonists of the invention may be administered in combination with a pharmaceutically acceptable carrier, such as isotonic saline, phosphate buffer solution or the like. Topical administration is feasible for those preferred peptides that are relatively small.

Compositions and excipients useful for the administration of small peptides through the nasal mucosa are, for example, described by U.K. patent application no. 8719248, published Feb. 24, 1988, applicant Sandoz Limited. Topical compositions with enhanced penetration through intact skin preferably include a potentiator, many of which are described by U.S. Pat. No. 4,091,090, issued May 23, 1978, inventor Sipos.

The peptides form pharmaceutically acceptable salts and can be administered in salt form. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, fumaric, succinic, tartaric, lactic, gluconic, ascorbic, maleic, benzenesulfonic, methane- and ethanesulfonic, hydroxymethane- and hydroxyethanesulfonic. Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine and lysine; guanidine; N-methylglucosamine; N-methylglucamine; L-glutamine; N-methylpiperazine; morpholine; ethylenediamine; N-benzylphenethylamine; tris (hydroxymethyl)aminomethane; and the like. (See for example, "Pharmaceutical Salts," $J.\ Pharm.\ Sci.,$ 66:1, pp. 1–19, 1977.)

For many applications, the peptide will preferably be formulated so as to enhance bioavailability. For example, U.S. Pat. No. 5,514,670, issued May 7, 1996, describes emulsions with a plurality of submicron particles, a bioactive peptide, and an aqueous continuous phase so as to enhance oral bioavailability of the peptide. Controlled release liposomal liquid pharmaceutical formulations for injection or oral administration are described in U.S. Pat. No. 4,016,100, and other liposomal/peptide compositions are described by U.S. Pat. No. 4,348,384. These three, just-noted patents are incorporated herein by reference.

EXAMPLE 5

Protein Synthesis

The protein fragment of human ARP consisting of residue (83–132) in an amidated form was synthesized on an Applied Biosystem's 433A automated peptide synthesizer (Foster City, Calif.) using hydroxymethyl or paramethyl benzylhydrylamine resin as the solid support and standard solid-phase F-moc methods. N-terminal F-moc amino acids were deprotected with piperidine in dimethylformamide (20% v/v) and coupled using o-benzotriazole-N,N,N',N'-tetramethyl-uronium hexafluorophosphate in 1-hydroxybenzotriazole (1:1 molar equivalents, in a 0.5 molar excess). The protein fragment was cleaved from resin with hydrogen fluoride containing anisole (13% v/v) and dimethyl sulfide (1.7% v/v) for 45 minutes at 0°C., washed with ethyl ether, and extracted with water/acetonitrile (50% v/v). The ARP-(83–132)-$NH_2$ fragment was cyclized in an acetonitrile/$NH_4HCO_4$ solution adjusted to pH 8.5 with ammonium hydroxide for 72 hours, and extracted with Bio-Rex 70 cation exchange resin for 24 hours. The Bio-Rex resin was then rinsed with $H_2O$, cyclized protein eluted from the resin with 50% glacial acetic acid in $H_2O$ (v/v), and analyzed by Pauly spray. Major fractions were purified by HPLC using a C-18 column over a standard 100% $H_2O$ (0.1% trifluoroacetic acid) to 100% acetonitrile (0.1% trifluoracetic acid) gradient, rotoevaporated, and lyophilized. Samples were then analyzed using matrix assisted laser desorption ionization-time of flight (MALDI-TOF) and electrospray mass spectrometry.

Testing Synthetic ARP Fragments for Functional Antimelanotropic Activity

Synthetic human ARP fragments were assayed for antagonist activity using $Xenopus\ laevis$ dermal melanophore cell preparations as described by Quillan et al., $Proc.\ Natl.\ Acad.\ Sci.\ USA,$ 92, pp. 2894–2898 (1995), and Quillan and Sadée, $Pharm.\ Res.,$ 14, pp. 713–719 (1997). Cultured melanophores can translocate cytoplasmic pigment vesicles in response to hormonal stimulation by a α-MSH, norepinephrine, vasotocin, pituitary adenylylcyclase activating peptide (PACAP), and serotonin. These compounds cause pigment dispersion and cell darkening. Pigment aggregation and cell lightening can be stimulated by melatonin. Melanophore responses were determined by measuring absorbance (OD) ratios taken through a monolayer of cells using a FisherBiotec BT2000 Microplate Reader (Pittsburgh, Pa.). Absorbance was measured before and after a 90 minute exposure to test peptides and then expressed as percent of initial absorbance. (Measurements were taken after 60 minutes pretreatment with 10 nM melatonin to initiate readings from an aggregated state.)

Protein Synthesis and Mass Spectra Analysis

Preparatory HPLC separations of synthetic extracts yielded protein fragments which were 99% pure by analytical HPLC. MALDI-TOF mass spectrometric analysis of the linear ARP fragments gave a molecular mass of 2984.5 daltons for (25–51) and 3282.5 daltons for (54–82), both of which correspond to expected theoretical values. The molecular mass of cyclized ARP-(83–132)-$NH_2$ as determined by MALDI-TOF and electrospray mass spectra was 5678.04 (SE 0.1%) and 5677.0 (SE 0.01%) daltons, respectively. These values are consistent with the calculated theoretical mass of 5676.7 daltons for protein containing a full complement of five disulfide bonds.

Antagonist Activity of the ARP Fragment

Synthetic ARP-(83–132)-$NH_2$ produced a dose-dependent suppression of α-MSH-induced dispersion of pigment in melanophore cells. The inhibitory equilibrium dissociation consent ($K_i$) of human ARP(83–132)-$NH_2$ as determined by Schild regression analysis, was 0.7 (SE 0.4) nM, which is comparable to $K_d$ values reported for ASP and ARP purified by recombinant means. Each of the three protein fragments had no "agonist like" activity in melanophore cells; when applied to melanophores in the absence of α-MSH they did not cause pigment dispersion in the presence of 10 nM melatonin. The specificity of ARP for MC receptor-mediated response was tested by examining ARP (83–132)-$NH_2$ for interaction with other ligands known to induce pigment dispersion. ARP(83–132)-$NH_2$ (30 nM) had no effect on concentration-response curves evoked with norepinephrine, serotonin, PACAP-27, and $Arg^8$-vasotocin, indicating that antagonism is selectively directed towards responses initialized by α-MSH stimulation of MC receptors.

These results demonstrate that a synthetic fragment of human ARP based on the amino acid sequence (83–132) can potently antagonize MC receptor function in Xenopus melanophores.

Electrospray mass spectrometry is a very accurate method of determining protein molecular mass and purity, but proteins containing disulfide bonds can produce multiply charged ions and fragment ions. This problem is accentuated with ARP(83–132)-$NH_2$ because of its multiple disulfide sites. Although the major peak in the electrospray mass spectrum was 5677.0 daltons, it contained a number of minor peaks not amenable to easy interpretation. None of the peaks, however, were consistent with protein containing less than five disulfide bonds; this was expected since cyclization reactions usually proceed to completion. To help better resolve the origin of the minor peaks we retested ARP (83–132)-NH$_2$ using MALDI-TOF mass spectrometry, a procedure less prone to fragmentation, and found only one major peak around 5678.04, which roughly corresponded to the expected theoretical mass of 5676.7 daltons. Although less precise, MALDI-TOF confirmed that minor peaks seen with the electrospray procedure were likely due to fragmentation. Thus, an ARP(83–132)-NH$_2$ structure containing a full complement of disulfide bonds appears to account for the biological activity observed in Xenopus melanophores.

It is to be understood that while the invention has been described above in conjunction with preferred specific embodiments, the description and examples are intended to illustrate and not limit the scope of the invention, which is defined by the scope of the appended claims.

What it is claimed:

1. A method for inhibiting activity of melanocytes, comprising:

administering to the melanocytes a melanocortin receptor antagonist, the antagonist with the sequence $Xaa^6$-$Arg^7$-$Xaa^8$-$Arg^9$-$Pro^{10}$-$Xaa^{11}$-$Xaa^{12}$, where $Xaa^6$ is Arg or D-Arg, Ala or D-Ala, $Xaa^8$ is Ile or Ala, $Xaa^{11}$ is Lys or D-Lys, and $Xaa^{12}$ is amidated Leu, D-Leu, or Ala, and $Arg^9$ may be in the D-Arg configuration, and wherein (a) if $Xaa^6$ is not in a D-configuration then $Arg^9$ is D-Arg, (b) the N-terminus is anisoylated, or both (a) and (b), and being in an amount effective at concentrations of less than 250 nM to block a determinable action of α-melanocyte stimulating hormone on *Xenopus laevis* melanophores or on mammalian cells transfected with melanocortin receptors.

2. The method as in claim 1 wherein the antagonist is a peptide in an emulsion adapted to enhance bioavailability thereof.

3. The method as in claim 1 wherein the melanocyte cells include a plurality of MCR-1 receptors.

4. The method as in claim 3 wherein the melanocyte receptor antagonist administered is selective for the MCR-1 receptor.

5. The method as in claim 1 wherein the antagonist is amidated at the C-terminus.

6. The method as in claim 1 wherein the peptide is p-anisoyl-dynorphin A(6–12)-$NH_2$.

7. The method as in claim 1 wherein the antagonist administered is encapsulated in liposomes.

8. The method as in claim 1 wherein the administration is therapeutically effective in inhibiting melanoma.

9. The method as in claim 8 wherein the administration is by topical application, injection, or oral administration.

* * * * *